United States Patent
Oh et al.

(10) Patent No.: US 11,617,619 B2
(45) Date of Patent: Apr. 4, 2023

(54) SYSTEM AND METHOD FOR DETECTING APPLICATION OF GROUNDING PAD FOR ABLATION DEVICES

(71) Applicant: Advanced Neuromodulation Systems, Inc., Plano, TX (US)

(72) Inventors: Seil Oh, Dallas, TX (US); Binesh Balasingh, Prosper, TX (US); William Winstrom, Leander, TX (US)

(73) Assignee: Advanced Neuromodulation Systems, Inc., Plano, TX (US)

( * ) Notice: Subject to any disclaimer, the term of this patent is extended or adjusted under 35 U.S.C. 154(b) by 226 days.

(21) Appl. No.: 17/089,325

(22) Filed: Nov. 4, 2020

(65) Prior Publication Data
US 2022/0133406 A1 May 5, 2022

(51) Int. Cl.
| | |
|---|---|
| *A61B 18/16* | (2006.01) |
| *G01R 31/68* | (2020.01) |
| *A61B 18/14* | (2006.01) |
| *A61B 18/00* | (2006.01) |
| *A61B 18/12* | (2006.01) |

(52) U.S. Cl.
CPC .............. *A61B 18/16* (2013.01); *G01R 31/68* (2020.01); *A61B 18/1492* (2013.01); *A61B 2018/00577* (2013.01); *A61B 2018/00654* (2013.01); *A61B 2018/00875* (2013.01);
(Continued)

(58) Field of Classification Search
CPC . A61B 18/1206; A61B 18/1492; A61B 18/16; A61B 2018/00339; A61B 2018/00577; A61B 2018/00654; A61B 2018/00875; A61B 2018/00892; A61B 2018/00916; A61B 2018/124; A61B 2018/1253; A61B 2018/126;
(Continued)

(56) References Cited

U.S. PATENT DOCUMENTS

| | | |
|---|---|---|
| 3,771,269 A | 11/1973 | Lerch et al. |
| 7,344,533 B2 | 3/2008 | Pearson et al. |

(Continued)

FOREIGN PATENT DOCUMENTS

WO  2019109334 A1  6/2019

OTHER PUBLICATIONS

International Search Report and Written Opinion, PCT/US2021/057282, dated Mar. 2, 2022, 10 pages.

*Primary Examiner* — Khadijeh A Vahdat
(74) *Attorney, Agent, or Firm* — Armstrong Teasdale LLP

(57) ABSTRACT

Disclosed herein is an RF ablation system including a plurality of electrodes, a ground pad, and a signal generator. The electrodes are positioned at respective tissue sites within a patient's body, and the ground pad is positioned on the patient's body. The signal generator is coupled to the ground pad and the electrodes via corresponding channels including a selected channel and unselected channels. The signal generator commutates switching circuits for the corresponding channels to close the selected channel and to open the unselected channels, and measures a first impedance over the selected channel. The signal generator commutates the switching circuits to close the selected channel and the unselected channels, and then measures a second impedance. The signal generator computes a difference between the first and second impedances, and determines the ground pad has at least a poor electrical connection to the patient's body when the difference exceeds a threshold.

19 Claims, 6 Drawing Sheets

(52) U.S. Cl.
CPC ............... *A61B 2018/00892* (2013.01); *A61B 2018/00916* (2013.01); *A61B 2018/126* (2013.01); *A61B 2018/167* (2013.01)

(58) Field of Classification Search
CPC ...... A61B 2018/1425; A61B 2018/143; A61B 2018/167; G01R 31/68
See application file for complete search history.

(56) References Cited

U.S. PATENT DOCUMENTS

| | | |
|---|---|---|
| 7,736,357 B2 | 6/2010 | Lee et al. |
| 9,119,533 B2 | 9/2015 | Ghaffari |
| 9,233,241 B2 | 1/2016 | Long |
| 2008/0051777 A1 | 2/2008 | Haemmerich |
| 2012/0089140 A1 | 4/2012 | Dunning et al. |
| 2015/0320480 A1 | 11/2015 | Cosman et al. |
| 2015/0351836 A1 | 12/2015 | Prutchi |

SYSTEM AND METHOD FOR DETECTING APPLICATION OF GROUNDING PAD FOR ABLATION DEVICES

FIELD

The present disclosure relates generally to ablation systems. In particular, the present disclosure relates to a system and method for detecting application of a grounding pad for radio frequency ablation systems.

BACKGROUND

Ablation therapy is a process by which target tissue of a patient is partially or completely damaged. Ablation may be achieved by a variety of techniques, such as chemical ablation, cryoablation, laser ablation, or radio frequency (RF) ablation. RF ablation, which utilizes RF signals in the frequency range of 375 kilohertz (KHz) to 500 KHz, can be used to treat various conditions afflicting the human anatomy. RF nerve ablation may be used, for example, to treat pain, such as osteoarthritic pain of the spine. RF ablation therapy reduces pain through the destruction of nerves using RF energy. RF ablation therapy may also be used, for example, to treat cardiac arrhythmias or hypertension.

The amount, or intensity, of the RF energy can be tuned for a particular cannula size, target tissue temperatures, and dwell time. For example, certain anatomical targets generally require a relatively large cannula and relatively large amounts of RF energy to create a relatively large lesion. Conversely, other anatomical targets may require less RF energy and a smaller cannula to limit collateral damage, i.e., to surrounding tissue. RF ablation generally involves the application of RF energy to target tissue by one or more electrodes connected to an RF signal generator, or an ablation generator. When the target tissue is ablated, or at least subjected to ablative energy generated by the RF generator, lesions form in the tissue. The one or more electrodes may be incorporated, for example, onto a catheter that can be navigated to the target tissue or, alternatively, onto respective needles that can each be inserted into corresponding target tissue. The electrodes deliver current to the target tissue to generate an electric field that heats the surrounding tissue and, with enough current, damages the tissue.

RF ablation operates by delivering current to target tissue, and that current must have a return path from the patient to electrical ground either through the signal generator or to ground directly. The ground path may be provided, for example, by another electrode on a catheter. More often the ground path is provided by a cutaneous patch electrode, or "ground pad," which may be applied, for example, to the thigh of the patient. The objective of the ground pad is to provide a good electrical connection between its one or more contacts and the patient. An improperly applied or loose ground pad, or a damaged contact, can result in increased impedance in the ground path at the application site, which can further result in heating at the application site and undesired burns or lesions. Some ground pads incorporate redundant contacts to ensure at least one contact makes a good electrical connection. However, single-contact ground pads are more common given their simplicity and lower cost. Accordingly, it is critical to ascertain whether the ground pad is properly attached with a good electrical connection when performing electric field-based ablation therapy, such as RF ablation.

SUMMARY OF THE DISCLOSURE

The present disclosure is directed to systems and methods that provide detection of ground pad placement in time-multiplexed electric field-based ablation systems, such as RF ablation systems.

The present disclosure is further directed to an RF ablation system including a plurality of electrodes, a ground pad, and a signal generator. The electrodes are configured to be positioned at respective tissue sites within a patient's body, and the ground pad is positioned on the patient's body to provide a ground path. The signal generator is coupled to the ground pad and the electrodes via corresponding channels that include a selected channel and a plurality of unselected channels. The signal generator commutates switching circuits for the corresponding channels to close the selected channel and to open the plurality of unselected channels, and measures a first impedance over the selected channel. The signal generator commutates the switching circuits to close the selected channel and the plurality of unselected channels, and then measures a second impedance over the selected channel. The signal generator computes a difference between the first and second impedances, and determines the ground pad has at least a poor electrical connection to the patient's body when the difference exceeds a threshold.

The present disclosure is further directed to a method of detecting placement of a ground pad for a radio frequency (RF) ablation system. The method includes commutating switching circuits of a signal generator for corresponding channels to close a selected channel and to open a plurality of unselected channels. The method includes measuring a first impedance over the selected channel, through an electrode and a patient's body, and through a ground path established by a ground pad. The method includes commutating the switching circuits to close the selected channel and the plurality of unselected channels. The method includes measuring a second impedance over the selected channel. The method includes computing a difference between the first impedance and the second impedance. The method includes determining the ground pad has at least a poor electrical connection to the patient's body when the difference exceeds a threshold.

The present disclosure is further directed a signal generator for radio frequency (RF) ablation therapy. The signal generator includes a ground terminal, a plurality of channels, a plurality of switching circuits, and a microcontroller. The ground terminal is configured to be coupled to a ground pad for application to a patient's body. The plurality of channels is configured to be coupled to corresponding electrodes for placement in the patient's body to form corresponding RF circuits. The plurality of channels include a selected channel and a plurality of unselected channels. The plurality of switching circuits correspond to the plurality of channels and each is configured to open and close the corresponding RF circuits. The microcontroller is configured to commutate the plurality of switching circuits to close the selected channel and to open the plurality of unselected channels. The microcontroller is configured to compute a first impedance over the selected channel. The microcontroller is configured to commutate the plurality of switching circuits to close the selected channel and the plurality of unselected channels. The microcontroller is configured to compute a second impedance over the selected channel. The microcontroller is configured to compute a difference between the first impedance and the second impedance, and determine the ground pad has at least a poor electrical connection to the patient's body when the difference exceeds a threshold.

BRIEF DESCRIPTION OF THE DRAWINGS

Corresponding reference characters indicate corresponding parts throughout the several views of the drawings. The drawings are not necessarily to scale.

DETAILED DESCRIPTION OF THE DISCLOSURE

Figure 1:
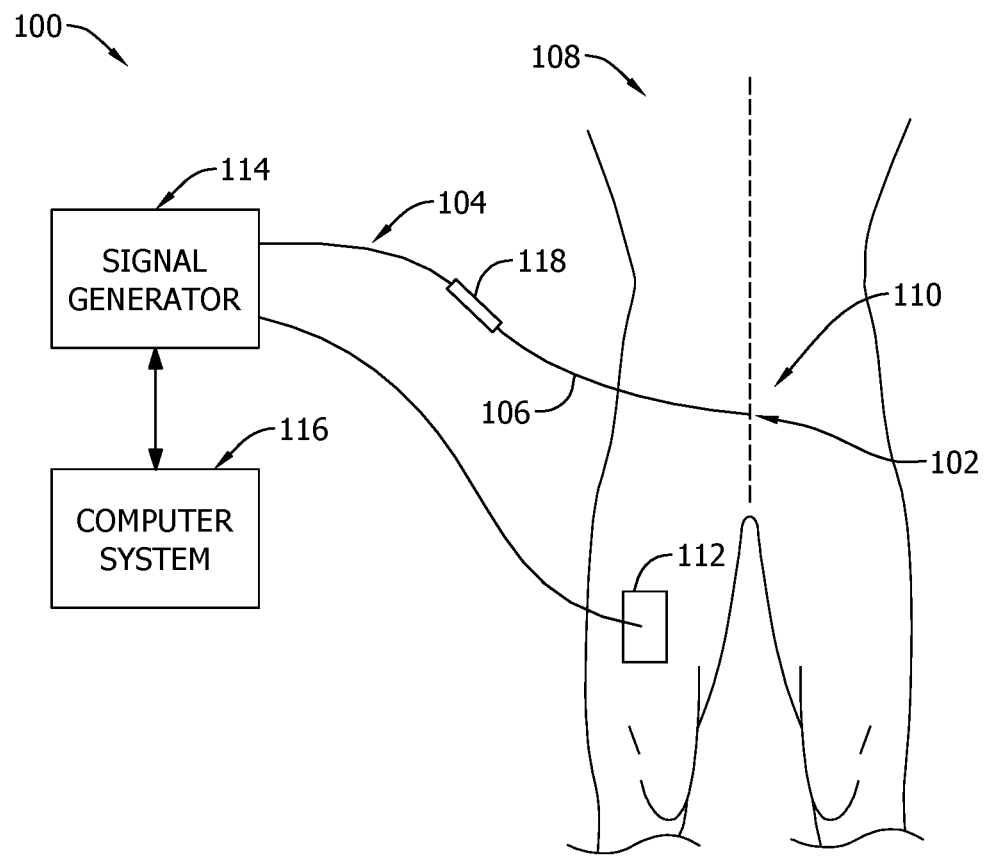
FIG. 1 is a schematic and block diagram view of an example RF ablation system.

RF ablation systems often utilize multiple electrodes to deliver ablation energy to multiple tissue sites in the anatomy of the patient. The ablation signal generator generally includes multiple channels for generating the respective RF signals to be delivered through the electrodes. The voltage, current, frequency, and duration of the application of the signals, in combination with the electrical load of the tissue itself, dictate the effect of the ablative energy on the target tissue, as well as surrounding tissue. The basic waveform of each RF signal is a high frequency (e.g., 375 KHz to 500 KHz) sinusoidal voltage (or current) waveform, and that waveform is applied, or pulsed, for a pulse duration, or pulse width. For example, the RF signal may be applied for a duration of 30 ms, with another duration between pulses, referred to as inter-pulse delay. The pulse width and inter-pulse delay are adjustable to treat a specific patient and specific target tissue. Generally, an operating range exists for the combination of RF signal properties that will deliver, at a lower bound, minimum ablative energy to form the desired lesions and, at an upper bound, maximum ablative energy to avoid damaging the wrong tissue. When treating with multiple ablation electrodes simultaneously, these boundaries apply in the aggregate. For example, there is an aggregate current limit for ablative energy through the multiple electrodes at a given instant in time. Moreover, appropriate timing of the RF pulses (e.g., pulse width and interpulse delay) can improve tissue selectivity, reduce musculoskeletal stimulation, and avoid certain side effects of treatment, such as burns and gas buildup.

Electric field-based ablation systems, such as RF ablation systems, require a ground path be established from the patient to allow current to conduct through the patient's tissue with a relatively low-impedance return path. The ground path could be made, for example, directly from the patient to an Earth ground. Alternatively, the ground path can be provided through the ablation signal generator itself. In either case, the ground path is often established using a ground pad attached to the skin of the patient, for example, on the patient's thigh. Because the RF signals can damage tissue at the application site of the ground pad if there is an improperly applied, or loose fitting, ground pad, or a damaged contact within the ground pad, it is important to ascertain whether the ground pad is attached with a good electrical connection before delivering ablative energy to the patient.

A common method of detecting whether a ground pad is properly attached with a good electrical connection is to measure and evaluate the impedance of the RF circuit formed by the electrode and its lead, the patient's body, and the ground pad. Many signal generators can make these measurements and evaluations before beginning ablation therapy. For example, a calibrated low-power signal is transmitted from a channel of the signal generator, the current conducts from the corresponding electrode, through the patient's body, and returns via the ground path. The current and voltage are measured, and the impedance is computed. Generally, if the ground pad is properly attached with a good electrical connection, the impedance of that connection should be very low (e.g., no more than 50 ohm). If the electrical connection at the ground pad is open or poor, the impedance at that connection should be very high, like an open circuit (e.g., above 10,000 ohm). The ablation load in the patient's tissue will depend on the location of the ablation electrode. For example, blood is a relatively good conductor, while other tissue is of higher impedance. Consequently, depending on the location of the ablation electrode, the ablation load may range from about 100 ohm to several kiloohm. Accordingly, the signal generator can detect the large impedance (e.g., above 10,000 ohm) when the ground pad is improperly applied or has a poor electrical connection.

At least some RF ablation systems utilize time-multiplexing of the numerous signal generator channels, which enables delivery of maximum power through each electrode, i.e., maximum power through an enabled electrode, and ideally no power through disabled electrodes. The energization strategy for such systems then cycles through each channel periodically, enabling application of the RF signal to the enabled channel for a selected pulse width, after which it is disabled and another channel is enabled for the selected pulse width. Pulse width in such an energization strategy may vary for each patient, as will the inter-pulse delay. For example, in one embodiment, the time-multiplexing may apply the RF signal from a first channel to a first electrode for a 30 ms pulse width, and then it is disabled while the signal generator cycles through each other channel for their corresponding pulse widths, which may be the same or different than the 30 ms pulse width for the first channel.

Time-multiplexing of the signal generator channels can be accomplished, for example, by introducing an RF switching circuit in series with each channel's output lead. Each RF switching circuit may include one or more semiconductor switching devices that interrupt the RF signal generated by the signal generator. Such semiconductor switching devices may include a metal-oxide semiconductor field-effect transistors (MOSFET), an insulated gate bipolar transistor (IGBT), or other solid state device. In an "ideal circuit," when an RF switching circuit is open, its impedance would be infinite. In practice, or in "non-ideal circuits," the RF switching circuit, particularly at high frequencies, such as RF, a capacitive leakage path exists through the device when it is open.

The leakage path through opened channels generally disrupts the assessment of the ground pad. More specifically, when measuring the impedance over a single channel, instead of measuring the series impedance of that channel to ground (the ideal circuit), the signal generator drives the calibrated low-power signal over multiple parallel paths to ground through the leakage paths of each open channel in addition to the series impedance of the closed channel. When the ground pad has a good electrical connection, the signal generator detects the intended impedance to ground through the ground pad (e.g., about 50 ohm) in parallel with each leakage path through the opened channels, each of which includes an ablation load and the impedance of the leakage path through the switching circuit. The relatively high-impedance leakage paths have little impact on the total impedance detected by the signal generator when the ground pad is properly applied and a good electrical connection to ground exists. However, when the ground pad is improperly applied or the electrical connection to ground is open or poor, the detected impedance will be that of the multiple parallel leakage paths through the opened channels, each of which is in the range of about 800 ohm to 5,000 ohm, depending on the type and condition of the target tissue, i.e., the ablation load. Consequently, even when the ground pad is improperly applied, has a poor electrical connection, or open, the impedance to ground is well below the threshold for determining the ground pad is not in place. For example, the detected impedance may be several hundred ohm or even several thousand ohm, while the threshold for detection may be 10,000 ohm.

The disclosed systems and methods provide detection of ground pad placement in time-multiplexed electric field-based ablation systems, such as RF ablation systems. The calibrated low-power signal is transmitted by the signal generator over a selected channel with all other unselected channels open, i.e., the respective switching circuits are open, and the impedance is measured. The calibrated low-power signal is transmitted again with all channels closed, i.e., all of the respective switching circuits are closed, and the impedance is measured again. The two impedance measurements are compared, and if the difference is above a certain threshold (e.g., 166 ohm), then the signal generator determines the ground pad is not properly applied, is missing entirely, or at least has a poor electrical connection. For example, when the ground pad is in place, the difference between the impedance measurements may be up to several tens of ohms or possibly up to 200 ohms, because the unselected channels are either relatively high-impedance leakage paths in parallel to the primary ground path through the ground pad, which is a low impedance (e.g., at most 50 ohm), or low-impedance closed circuits in parallel to the primary ground path through the ground pad. And when the ground pad is improperly applied, open, or at least has a poor electrical connection, the difference between the impedance measurements may be several hundred ohms, because the unselected channels are the only ground path, or are approximately the lowest impedance ground path. Consequently, when the unselected channels are open, there is no lower impedance (e.g., less than 50 ohm) ground path than the parallel leakage paths, and the parallel impedance may be equivalent to several hundred ohms or more. And when the unselected channels are closed, they provide multiple parallel low-impedance ground paths, which may be equivalent to several tens of ohms or up to 200 ohms. Thus, the difference between the impedance measurements will be on the order of several hundreds of ohms, versus tens of ohms, or up to 200 ohms, when the ground pad is in place.

Figure 2:
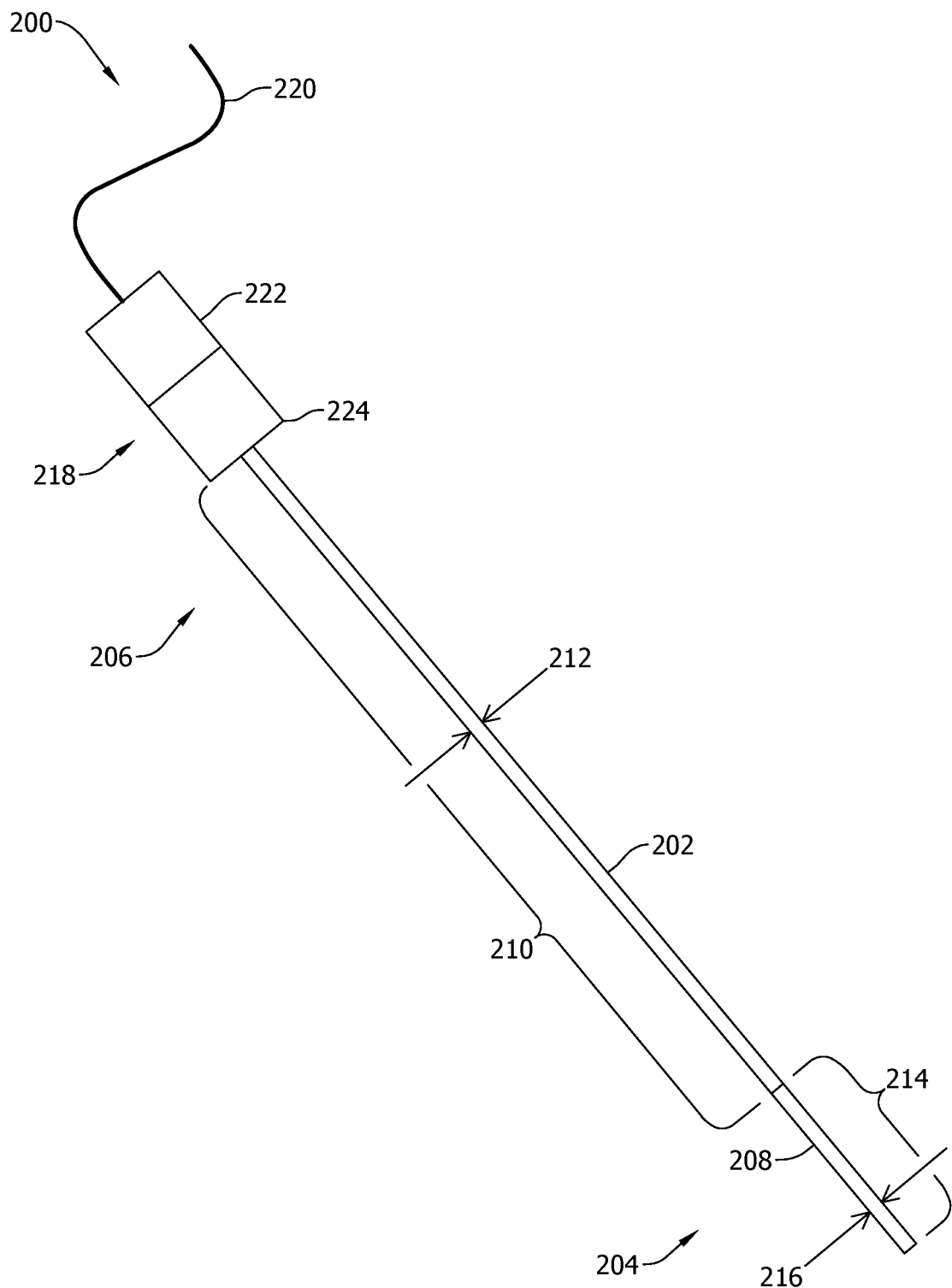
FIG. 2 is a schematic diagram of an example ablation needle for use with the RF ablation system shown in FIG. 1.

The disclosed systems and methods are generally embodied in an electric field-based ablation system, such as an RF ablation system. FIG. 1 illustrates an example embodiment of a system 100 for RF ablation therapy. Certain embodiments, such as system 100, include an electrode assembly 102 disposed at the distal end, for example, of an ablation lead 104 and an ablation needle 106. As used herein, "proximal" refers to a direction toward the end of the ablation lead 104 near the clinician and "distal" refers to a direction away from the clinician and (generally) inside the body of a patient 108. In alternative embodiments, system 100 may include a plurality of needles having one or more electrodes at their respective distal ends (as shown in FIG. 2). Electrode assembly 102 includes one or more individual, electrically-isolated electrode elements. In some embodiments, each electrode element, also referred to herein as an ablation electrode, is individually wired such that it can be selectively paired or combined with any other electrode element to act as a bipolar or a multi-polar electrode.

Electrode assembly 102 includes a plurality of electrodes configured to be used as briefly outlined above and as described in greater detail below. Electrode assembly 102 is incorporated as part of ablation lead 104 used for RF ablation. System 100 introduces a modulated electric field into tissue 110 in a body of a patient 108. In the illustrative embodiment, tissue 110 comprises nerve tissue for the treatment of pain, e.g., chronic spinal pain. It should be understood, however, that embodiments may be used to diagnose or treat a variety of other body tissues.

System 100 enables RF ablation therapy to form lesions on target tissue 110. System 100 utilizes electric current in the form of an RF alternating current (AC) signal delivered by multiple electrodes on electrode assembly 102, or respective electrodes on a plurality of ablation needles (as shown in FIG. 2, for example). In alternative embodiments, system 100 may be used to perform electroporation therapy in which electric current is delivered as a pulsed electric field in the form of short-duration direct current (DC) pulses between closely spaced electrodes on electrode assembly 102. Pulse widths of these DC signals may be on the order of one nanosecond to several milliseconds, and the DC pulses may be repeated to form a pulse train. When a strong electric field is applied to tissue in vivo, the cells in the tissue are subjected to a trans-membrane potential that opens the pores on the cell wall, hence the term electroporation. Electroporation may be reversible (i.e., the temporally-opened pores will reseal) or irreversible (i.e., the pores will remain open). For example, in the field of gene therapy, reversible electroporation (i.e., temporarily open pores) is used to transfect high molecular weight therapeutic vectors into the cells. In other therapeutic applications, a suitably configured pulse train alone may be used to cause cell destruction, for instance by causing irreversible electroporation (IRE).

It should be understood that while the energization strategies for ablation are described as involving AC and/or DC waveforms, embodiments may use variations of AC or DC pulses and remain within the spirit and scope of the invention. For example, exponentially-decaying pulses, exponentially-increasing pulses, and combinations thereof may be used. Moreover, while certain embodiments of system 100 are described herein with respect to RF ablation therapy, it should be understood that system 100 may be used, additionally or alternatively, for other forms of electric field-based ablation therapy.

System 100 further includes a ground pad 112 that provides a ground path, for example, for RF signals transmitted by a signal generator 114 through electrode assembly 102 and into the body of the patient 108. In the illustrated embodiment, ground pad 112 is a cutaneous patch electrode. Likewise, system 100 may include additional return electrodes that may also be cutaneous patch electrodes. Although at least some ground pads may include two or more ground contacts, the disclosed systems and methods generally utilize a single contact in ground pad 112. In alternative embodiments, the systems and methods described herein may be expanded and modified to operate with dual contact ground pads, or ground pads having two or more ground contacts. In certain embodiments, return electrodes may be any other type of electrode suitable for use as a return electrode, or ground path, including, for example, one or more catheter electrodes. Return electrodes that are catheter electrodes may be part of another electrode assembly (not shown) or part of a separate catheter (not shown). In some embodiments, for example, system 100 includes a bipolar catheter electrode assembly that includes a plurality of electrode pairs, where each electrode pair includes two electrodes with one electrode functioning as the return electrode.

System 100 may further include a computer system 116 (e.g., including an electronic control unit and memory) Computer system 116 may further include conventional interface components, such as various user input/output mechanisms and a display, among other components.

System 100 may include a suitable detector and tissue sensing circuit integrated with signal generator 114 or computer system 116 that identify which electrodes of electrode assembly 102 have characteristics (e.g., electrical characteristics such as impedance, phase angle, reactance, etc.) indicative of contact with tissue 110. Signal generator 114 or computer system 116 may then select which electrodes or electrode pairs of electrode assembly 102 to energize based on the electrodes identified as being in contact with tissue 110. Suitable components and methods for identifying electrodes in contact with tissue are described, for example, in U.S. Pat. No. 9,289,606, the disclosure of which is incorporated herein by reference in its entirety.

It should be understood that electrode assembly 102 is not limited to the specific constructions shown and described herein, and may include any other suitable electrode assembly and have any other suitable construction that enables system 100 to function as described herein.

Signal generator 114 is a high-frequency signal generator configured to generate AC signals at an RF frequency in the range of about 350 kilohertz (KHz) and 500 KHz. For example, in certain embodiments, signal generator 114 generates AC signals at about 460 KHz. In alternative embodiments, signal generator 114 can generate various RF frequencies in the RF range. In some embodiments, signal generator 114 is configured to output energy in waveforms at selectable energy levels, such as fifty joules, one-hundred joules, two-hundred joules, and the like. Other embodiments may have more or fewer energy settings, and the values of the available settings may be the same or different. In alternative embodiments, signal generator 114 is a monophasic or biphasic signal generator configured to generate a series of DC pulses. For example, in some embodiments, signal generator 114 outputs or generates a pulse having a magnitudes between about 600 V and about 3.5 kV. Other embodiments may output or generate any other suitable voltage.

System 100 may include a variable impedance 118. The variable impedance 118 may be used to change one or more characteristics, such as amplitude, duration, pulse shape, and the like, of an output of signal generator 114. Although described as a separate component, the variable impedance 118 may be integrated with ablation lead 104 or signal generator 114. The variable impedance 118 may include one or more impedance elements, such as resistors, capacitors, or inductors connected in series, parallel, or combinations of series and/or parallel. The variable impedance 118 may be connected in series with ablation lead 104. Alternatively, the impedance elements of the variable impedance 118 may be connected in parallel with ablation lead 104 or in a combination of series and parallel. Moreover, in other embodiments, the impedance elements of the variable impedance 118 are connected in series and/or parallel with ground pad 112. Some embodiments include more than one variable impedance 118, each of which may include one or more impedance elements. In such embodiments, each variable impedance 118 may be connected to a different electrode or group of electrodes to allow the impedance through each electrode or group of electrodes to be independently varied. In other embodiments, the impedance of system 100 may not need to be varied and the variable impedance 118 may be omitted.

FIG. 2 is a schematic diagram of an example ablation needle 200 for use with RF ablation system 100 shown in FIG. 1. Ablation needle 200 includes an elongate body 202 having a distal end 204 for insertion into a patient's body, and a proximal end 206 configured to remain exterior to the body. An electrode 208 is positioned at distal end 204 such that, upon insertion, electrode 208 can be positioned at a tissue site for delivering ablative energy. Generally, elongate body 202 is electrically isolated from electrode 208 at distal end 204. To enable proper positioning of distal end 204, elongate body 202 may have any length 210 and diameter 212 suitable for reaching a given region of target tissue in a given patient's body. For example, a physician may utilize an ablation needle 200 having one length 210 and diameter 212 for performing renal denervation in a first patient, and a different length 210 and diameter 212 for performing the same procedure in a second patient. Likewise, electrode 208 may have various lengths 214 and diameters 216. Selection of length 214 and diameter 216 of electrode 208 may be based on various factors, including, for example, patient anatomy, type of target tissue, and the size of the lesion proscribed for the ablation therapy. The size of electrode 208 generally limits the amount of power that can be delivered through ablation needle 200, and also the surface area of tissue contact that can be achieved for ablation therapy. For example, a large electrode 208 may contact a greater tissue area, which generally increases the ablation load. The larger electrode 208 can also deliver more ablative energy and produce a larger lesion, but generally with less precision than a smaller electrode 208, and potentially requiring more total current to achieve ablative energy levels in the target tissue. In some RF ablation therapies, a smaller electrode 208 is desired to deliver more concentrated RF energy to a smaller region of tissue.

Proximal end 206 of elongate body 202 includes a connector assembly 218 that provides electrical coupling of ablation needle 200 to a lead wire 220. Lead wire 220 couples, directly or indirectly, to a channel of an ablation signal generator, such as signal generator 114 shown in FIG. 1. Connector assembly 218 may include a lead connector 222 and a needle connector 224 to enable mechanical and electrical separation of ablation needle 200 from lead wire 220 for easier insertion and removal from the patient's body. In alternative embodiments, connector assembly 218 may be fixed such that lead wire 220 and ablation needle 200 cannot be separated without destroying ablation needle 200, or at least not without significant effort or rendering ablation needle 200 permanently inoperable for therapeutic use.

Figure 3:
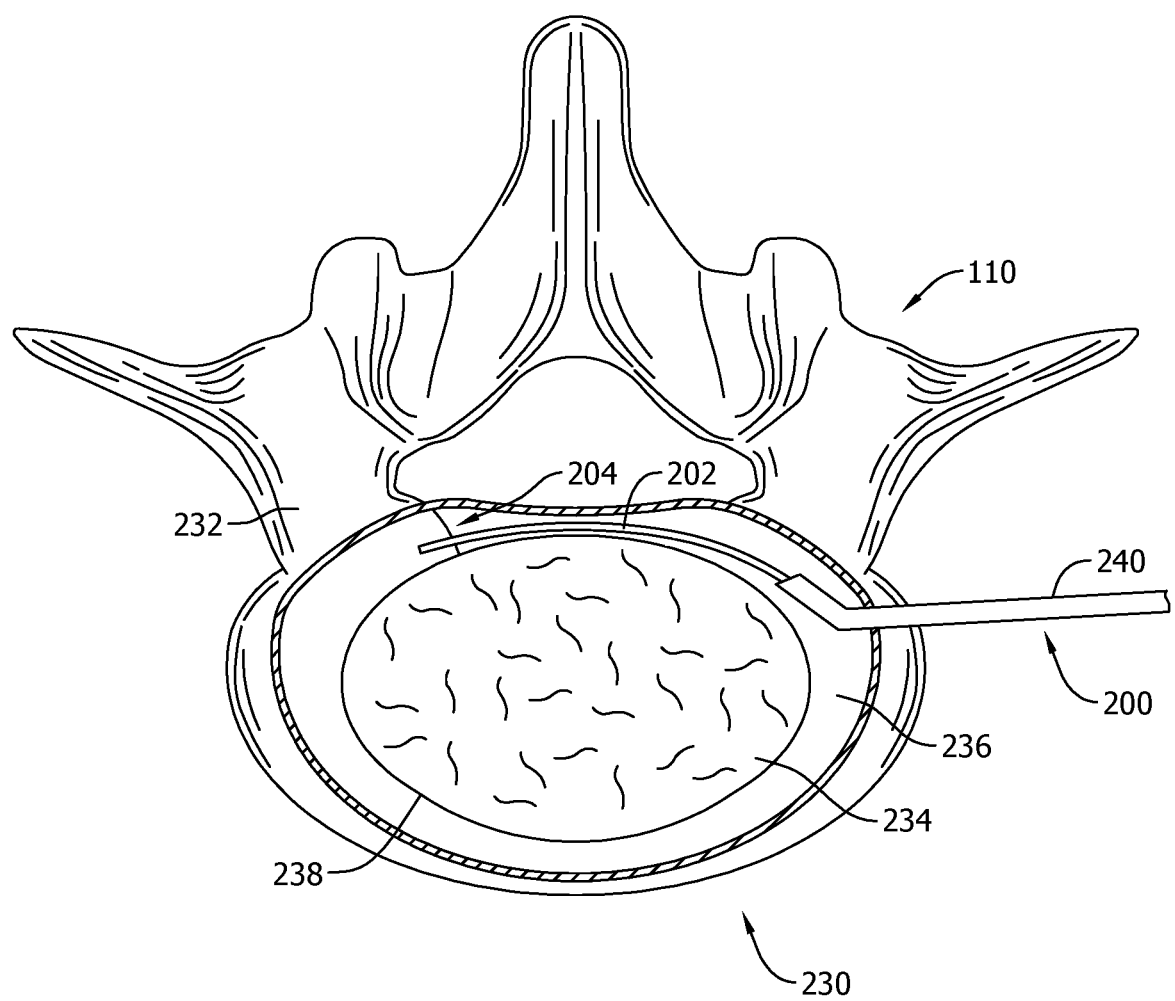
FIG. 3 is a cross-sectional illustration of the ablation needle shown in FIG. 2 placed proximate a disc of a patient's spine shown adjacent to a vertebra.

FIG. 3 is a cross-sectional illustration of ablation needle 200 placed proximate a disc 230 of a patient's spine shown adjacent to a vertebra 232. Generally, disc 230 includes a nucleus 234, an annular fibrosis 236, and a thin layer 238 defining an annular nuclear interface, or transitional, zone. Ablation needle 200 is illustrated positioned in the disc annulus, or annular fibrosis 236 for RF ablation therapy via an introducer needle 240. Alternatively, ablation needle 200 may be positioned in disc nucleus 234.

Figure 4:
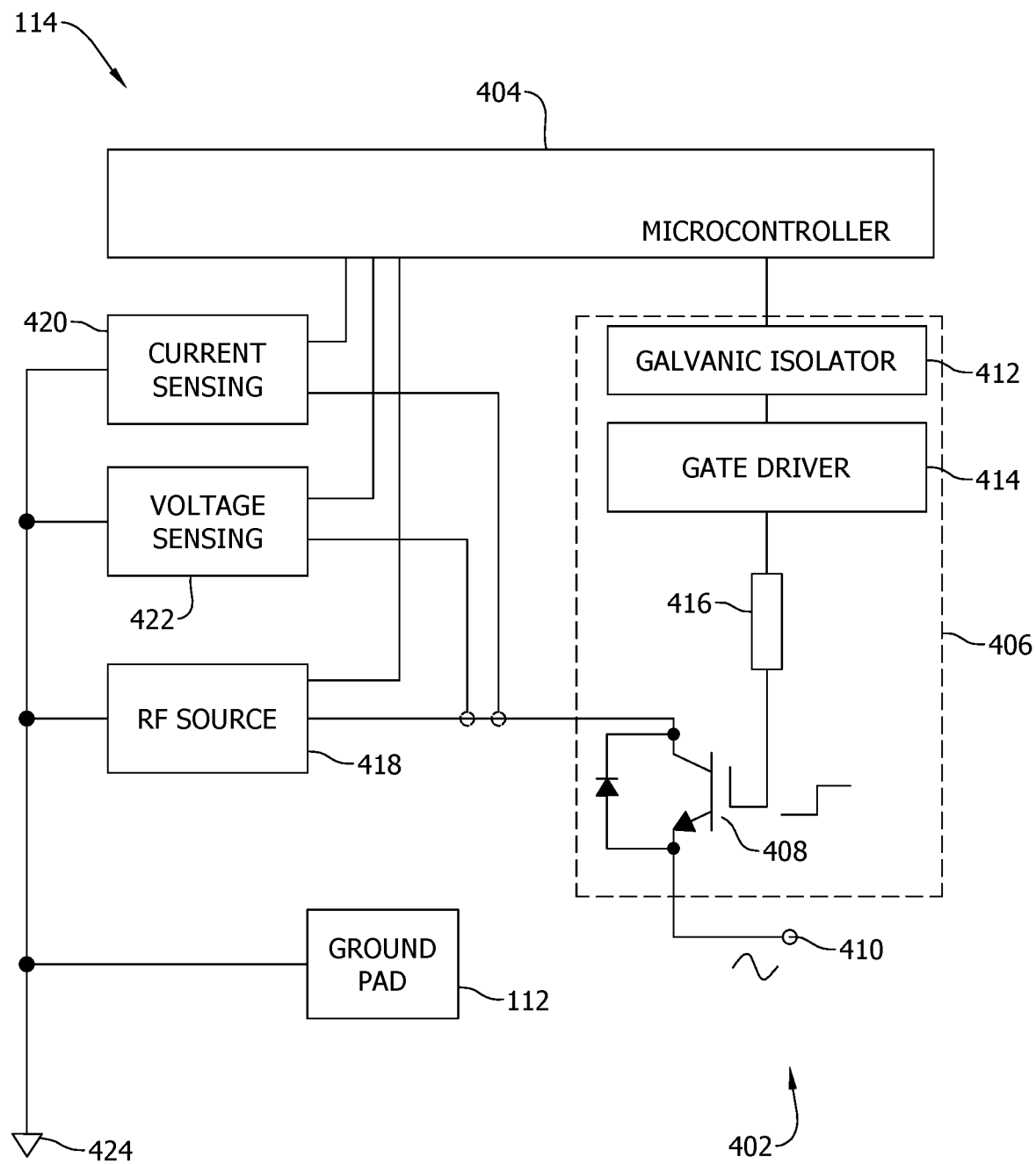
FIG. 4 is a schematic diagram of an example signal generator for use in the system shown in FIG. 1.

FIG. 4 is a schematic diagram of signal generator 114 shown in FIG. 1. Signal generator 114 includes a plurality of channels 402 for delivering ablative energy to the body of a patient 108 through, for example, ablation lead 104 or a plurality of ablation needles 200. FIG. 4 illustrates a single channel 402 for clarity, however signal generator 114 generally includes two or more channels. The plurality of channels 402 are time-multiplexed such that only a single channel 402 is active, or selected, at a given moment in time. Signal generator 114 includes a microcontroller 404 that controls each channel 402. For example, microcontroller 404 may include a plurality of digital output channels that each produce logic level DC signals to control respective switching circuits. More specifically, each switching circuit 406 includes one or more solid state switching device 408, such as a metal-oxide semiconductor field-effect transistor (MOSFET), insulated gate bipolar transistor (IGBT), or other suitable semiconductor device for making and breaking an RF circuit formed by signal generator 114, an electrode 410 for that channel 402, target tissue 16 in the body 17 of the patient, and ground pad 112. Microcontroller 404 is galvanically isolated from each switching circuit 406 by a galvanic isolator 412. The logic level DC signals pass through galvanic isolator 412 to a gate driver 414 that supplies suitable voltage and current to operate the gate of solid state switching device 408. Each switching circuit 406 may also include a gate impedance 416.

Signal generator 114 includes an RF source 418 that generates the RF signals that carry the ablative energy through solid state switching device 408 to electrodes 410, and through the body of the patient 108 to ground pad 112. In certain embodiments, signal generator 114 includes a plurality of RF sources 418 for driving the plurality of channels 402. RF source 418 may be controlled, for example, by microcontroller 404. Control of RF source 418 may include frequency, voltage amplitude, current amplitude, or phase. Microcontroller 404 also controls RF source 418 to detect proper application and electrical connection of ground pad 112, including, for example, the generation of a calibrated low-power signal that is transmitted through a selected channel 402 of the plurality of channels 402. The transmission through the selected channel 402 is controlled by microcontroller 404 and its control of switching circuits 406 for each channel 402. The low-power signal may be, for example, a 15 V RF signal applied for 10 ms. The voltage, current, frequency, and duration can be adjusted for a specific patient by controlling both RF source 418 and the switching circuit 406 for the selected channel 402 accordingly.

Signal generator 114 also includes a current sensing circuit 420 and a voltage sensing circuit 422. Current sensing circuit 420 is coupled to the plurality of channels 402 to enable sensing, or measuring, of current through each channel 402. Current sensing circuit 420 may include, for example, a shunt resistor or a hall effect sensor. Voltage sensing circuit 422 is coupled to the plurality of channels 402 to enable sensing, or measuring, of a root mean squared (RMS) voltage applied to each channel 402. Voltage sensing circuit 422 may include, for example, a voltage divider circuit for detecting the voltage applied to a given channel 402.

Signal generator 114 also includes a ground reference, or simply "ground," 224 to which RF source 418, current sensing circuit 420, and voltage sensing circuit 422 are referenced. Moreover, ground pad 112 provides a ground path back to the same ground 424 to close the RF circuits formed by each channel 402.

Figure 5:
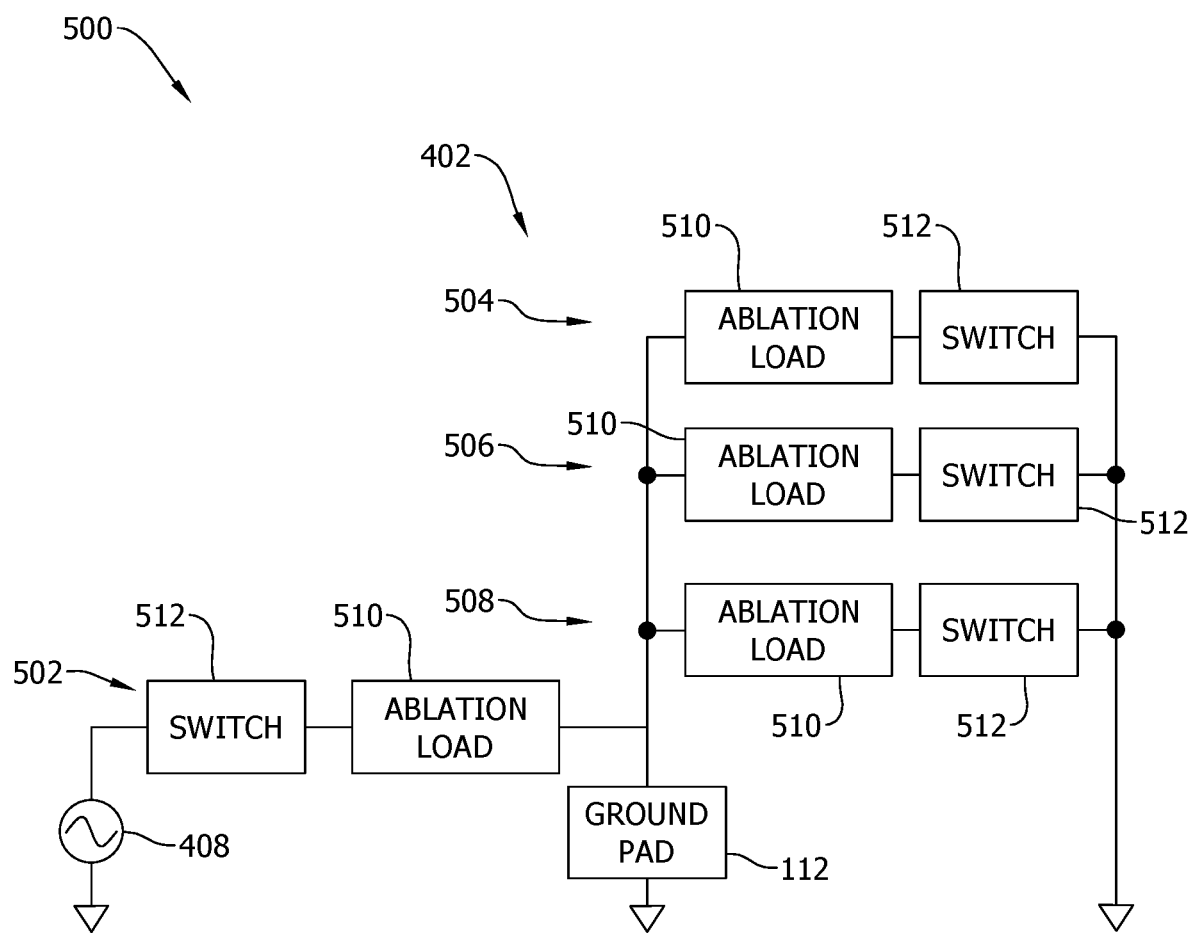
FIG. 5 is a circuit diagram of an RF circuit illustrating the impedances and ground paths in a time-multiplexed RF ablation system.

FIG. 5 is a circuit diagram of an RF circuit 500 illustrating the impedances and ground paths in a time-multiplexed RF ablation system. RF circuit 500 includes RF source 418 of signal generator 114 and a plurality of channels 402, including a selected channel 502 and unselected channels 504, 506, and 508. Each of the channels 402 (e.g., as shown in FIG. 4) is configured to supply ablative energy to target tissue 110 through a switching circuit 406 and, more specifically through solid state switching device 408. Accordingly, the RF circuit for each channel is composed of an ablation load 510 representing the impedance of tissue 110 at which a given electrode 410 is targeted, or positioned, and a switch impedance 512 representing the impedance of the solid state switching devices 408 in each switching circuit 406. RF circuit 500 also includes ground pad 112, which provides a ground path back to signal generator 114.

Each of the impedance components of RF circuit 500 has an impedance that varies depending on, for example, the positioning of the corresponding electrode 410 for a given channel 402 (i.e., the type and condition of the tissue at that site), the state of solid state switch devices 408, or the state of ground pad 112, i.e., the condition of its electrical connection to the body of the patient 108.

The impedance of ground pad 112 may be relatively low when it is properly applied, exhibiting a contact impedance of about 50 ohm or less. Conversely, when ground pad 112 is improperly applied, open, or has a poor electrical connection, the contact impedance is generally in excess of several thousand ohms, for example, above 10,000 ohms.

The switch impedances 512 of solid state switch devices 408 may be very low when the solid state switch device 408 is closed. For example, when closed, the switch impedance 512 may be 1 ohm or less. Conversely, when solid state switch devices 408 are open, switch impedance 512 is relatively high, often several hundred ohms. Notably, when open, switch impedance 512 is not so high as to function as an open circuit at high frequencies, e.g., RF frequencies in the range of 350 KHz to 500 KHz, due to the capacitive leakage current conducted through the solid state switch device 408. For example, in one embodiment, switch impedance 512 is about 800 ohms in the open state.

The ablation loads 510 of the tissue 110 of the patient vary based on the location, type of tissue, and the condition of the tissue. For example, the ablation load 510 may be as low as several tens of ohms (e.g., blood), or 1,000 or more ohms for other tissue.

Figure 6:
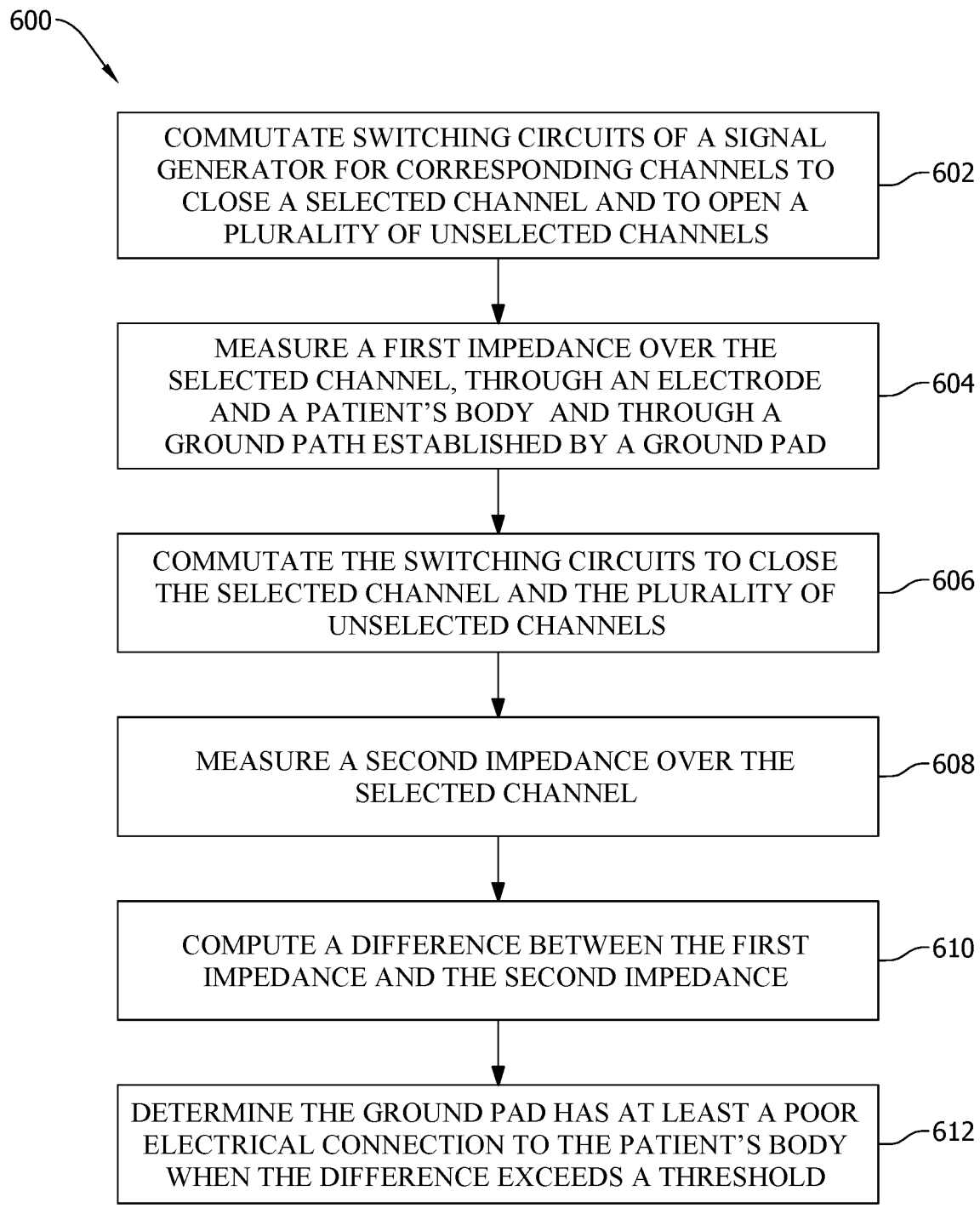
FIG. 6 is a flow diagram of an example method of detecting placement of a ground pad for an RF ablation system.

FIG. 6 is a flow diagram of an example method 600 of detecting placement of ground pad 112 for RF ablation system 100 shown in FIG. 1. The ground pad is a cutaneous patch having a single electrical contact for establishing a ground path from a patient's body and, more specifically, a return path back to signal generator 114 for creating the necessary electric fields in the tissue of the patient. A plurality of electrodes is placed at respective tissue sites in the patient's body. The electrodes may be integrated, for example, onto electrode assembly 102 of ablation lead 104 (shown in FIG. 1). Alternatively, each electrode may be disposed on a distal end of a corresponding ablation needle 200 (shown in FIG. 2). Once the electrode assembly 102 or ablation needles 200 are positioned, they are connected to corresponding channels 402 of signal generator 114.

Signal generator 114 generally will detect whether ground pad 112 is properly placed before enabling ablative energy to be generated. Microcontroller 404 controls switching circuits 406 to commutate 602 corresponding channels 402 to close selected channel 502 and to open a plurality of unselected channels, e.g., unselected channels 504, 506, and 508. A first impedance is then measured 604 over selected channel 502, through an electrode positioned in the patient's body, and through a ground path established by ground pad 112. Microcontroller 404 controls RF source 418 to transmit a low-power RF signal over selected channel 502. The low-power RF signal is generally generated at the therapeutic ablation frequency (e.g., 460 KHz) and supplied to selected channel 502 through its corresponding switching circuit 406 for a set duration. The duration of the low-power RF signal is generally brief enough to avoid accumulating enough RF energy in the tissue 110 to potentially burn, damage, or ablate the tissue 110. For example, the pulse duration may be in the range of 1 ms to several tens of ms, e.g., up to 100 ms. In one embodiment, for example, the low-power RF signal is "pulsed" for 10 ms.

The current conducted through selected channel 502 is measured by current sensing circuit 420, and an RMS voltage applied to selected channel 502 is measured by voltage sensing circuit 422. The first impedance is then computed based on the measured current and measured RMS voltage.

Switching circuits 406 are then commutated 606 to close selected channel 502 and the plurality of unselected channels 504, 506, and 508. A second impedance is then measured 608 over selected channel 502 in the same manner as the first impedance. Microcontroller 404 then computes 610 a difference between the first impedance and the second impedance, and determines 612 the ground pad 112 is either properly placed, or is not properly placed or at least has a poor electrical connection to the patient's body. When the difference exceeds a threshold (e.g., 166 ohms), microcontroller 404 determines ground pad 112 is not properly placed, open, or at least has a poor electrical connection. If the difference does not exceed the threshold, then ground pad 112 is in place with a good electrical connection.

When ground pad 112 is properly placed, microcontroller 404 controls switching circuits 405 to commutate to close selected channel 502 and to open the unselected channels 504, 506, and 508. Microcontroller 404 then enables transmission of an RF ablation signal over selected channel 502. Microcontroller 404 controls switching circuits 406 to time-multiplex the RF ablation signal over the plurality of channels 402.

Although certain steps of the example method are numbered, such numbering does not indicate that the steps must be performed in the order listed. Thus, particular steps need not be performed in the exact order they are presented, unless the description thereof specifically require such order. The steps may be performed in the order listed, or in another suitable order.

Although the embodiments and examples disclosed herein have been described with reference to particular embodiments, it is to be understood that these embodiments and examples are merely illustrative of the principles and applications of the present disclosure. It is therefore to be understood that numerous modifications can be made to the illustrative embodiments and examples and that other arrangements can be devised without departing from the spirit and scope of the present disclosure as defined by the claims. Thus, it is intended that the present application cover the modifications and variations of these embodiments and their equivalents.

Some embodiments involve the use of one or more electronic processing or computing devices. As used herein, the term "microcontroller" and related terms, e.g., "processor," "computer", "processing device," "computing device," and "controller," are not limited to just those integrated circuits referred to in the art as a computer, but broadly refer to a processor, a processing device, a controller, a general purpose central processing unit (CPU), a graphics processing unit (GPU), a microcontroller, a microcomputer, a programmable logic controller (PLC), a reduced instruction set computer (RISC) processor, a field programmable gate array (FPGA), a digital signal processing (DSP) device, an application specific integrated circuit (ASIC), and other programmable circuits or processing devices capable of executing the functions described herein, and these terms may be used interchangeably herein. These processing devices are generally "configured" to execute functions by programming or being programmed, or by the loading or other provisioning of instructions for execution. The above examples are not intended to limit in any way the definition or meaning of the terms processor, processing device, and related terms.

In the embodiments described herein, memory may include, but is not limited to, a non-transitory computer-readable medium, such as flash memory, a random access memory (RAM), read-only memory (ROM), erasable programmable read-only memory (EPROM), electrically erasable programmable read-only memory (EEPROM), and non-volatile RAM (NVRAM). As used herein, the term "non-transitory computer-readable media" is intended to be representative of any tangible, computer-readable media, including, without limitation, non-transitory computer storage devices, including, without limitation, volatile and non-volatile media, and removable and non-removable media such as a firmware, physical and virtual storage, CD-ROMs, DVDs, and any other digital source such as a network or the Internet, as well as yet to be developed digital means, with the sole exception being a transitory, propagating signal. Alternatively, a floppy disk, a compact disc-read only memory (CD-ROM), a magneto-optical disk (MOD), a digital versatile disc (DVD), or any other computer-based device implemented in any method or technology for short-term and long-term storage of information, such as, computer-readable instructions, data structures, program modules and sub-modules, or other data may also be used. Therefore, the methods described herein may be encoded as executable instructions, e.g., "software" and "firmware," embodied in a non-transitory computer-readable medium. Further, as used herein, the terms "software" and "firmware" are interchangeable, and include any computer program stored in memory for execution by personal computers, workstations, clients and servers. Such instructions, when executed by a processor, cause the processor to perform at least a portion of the methods described herein.

This written description uses examples to disclose the invention, including the best mode, and also to enable any person skilled in the art to practice the disclosure, including making and using any devices or systems and performing any incorporated methods. The patentable scope of the disclosure is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:

1. A radio frequency (RF) ablation system comprising:
a plurality of electrodes configured to be positioned at respective tissue sites within a patient's body;
a ground pad configured to be positioned on the patient's body to provide a ground path from the patient's body; and
a signal generator coupled to the ground pad and further coupled to the plurality of electrodes via corresponding channels, the corresponding channels including a selected channel and a plurality of unselected channels, the signal generator comprising switching circuitry configured to selectively open and close each of the corresponding channels, the signal generator configured to:
provide one or more control signals to reverse the switching circuitry for the corresponding channels to close the selected channel and to open the plurality of unselected channels;
measure a first impedance over the selected channel;
provide one or more control signals to reverse the switching circuitry to close the selected channel and the plurality of unselected channels;
measure a second impedance over the selected channel;
compute a difference between the first impedance and the second impedance; and
determine the ground pad has at least a poor electrical connection to the patient's body when the difference exceeds a threshold.

2. The RF ablation system of claim 1, wherein the threshold is in a range of 25 to 200 ohms.

3. The RF ablation system of claim 1, wherein the signal generator is further configured to measure the first impedance by transmitting a first low-power RF signal over the selected channel and measuring a current and a voltage, and computing the first impedance based on the current and voltage.

4. The RF ablation system of claim 1, wherein the signal generator is further configured to transmit an RF ablation signal over the selected channel.

5. The RF ablation system of claim 4, wherein the signal generator is further configured to time-multiplex the RF ablation signal over each of the corresponding channels.

6. The RF ablation system of claim 1, wherein the ground pad comprises only a single contact.

7. A method of detecting placement of a ground pad for a radio frequency (RF) ablation system, the RF ablation system including a plurality of electrodes configured to be positioned at respective tissue sites within a patient's body, a ground pad configured to be positioned on the patient's body to provide a ground path from the patient's body, and a signal generator coupled to the ground pad and further coupled to the plurality of electrodes via corresponding channels, the corresponding channels including a selected channel and a plurality of unselected channels, the signal generator including switching circuitry configured to selectively open and close each of the corresponding channels, the method comprising:
providing one or more control signals to reverse the switching circuitry to close the selected channel and to open the plurality of unselected channels;
measuring a first impedance over the selected channel;
providing one or more control signals to reverse the switching circuitry to close the selected channel and the plurality of unselected channels;
measuring a second impedance over the selected channel;
computing a difference between the first impedance and the second impedance; and
determining the ground pad has at least a poor electrical connection to the patient's body when the difference exceeds a threshold.

8. The method of claim 7, wherein measuring the first impedance comprises:
transmitting a first low-power RF signal over the selected channel;
measuring a current conducted through the selected channel and an RMS voltage applied to the selected channel; and
computing the first impedance based on the current and the RMS voltage.

9. The method of claim 8, wherein transmitting a first low-power RF signal comprises:
generating an RF signal at a therapeutic ablation frequency; and
supplying the RF signal to the selected channel.

10. The method of claim 7 further comprising determining the ground pad is properly applied when the difference does not exceed the threshold.

11. The method of claim 10 further comprising:
providing one or more control signals to reverse the switching circuitry to close the selected channel and to open the unselected channels; and
transmitting an RF ablation signal over the selected channel.

12. The method of claim 11 further comprising time-multiplexing the RF ablation signal over each of the corresponding channels.

13. The method of claim 7 further comprising placing the ground pad at a grounding site on the patient's body.

14. A signal generator for radio frequency (RF) ablation therapy, the signal generator comprising:
a ground terminal configured to be coupled to a ground pad for application to a patient's body;
a plurality of channels configured to be coupled to corresponding electrodes for placement in the patient's body to form corresponding RF circuits, the plurality of channels including a selected channel and a plurality of unselected channels;
a plurality of switching circuits corresponding to the plurality of channels and configured to open and close the corresponding RF circuits; and
a microcontroller configured to:
commutate the plurality of switching circuits to close the selected channel and to open the plurality of unselected channels;
compute a first impedance over the selected channel;
commutate the plurality of switching circuits to close the selected channel and the plurality of unselected channels;
compute a second impedance over the selected channel;
compute a difference between the first impedance and the second impedance; and
determine the ground pad has at least a poor electrical connection to the patient's body when the difference exceeds a threshold.

15. The signal generator of claim 14, wherein the threshold is in a range of 25 to 200 ohms.

16. The signal generator of claim 14 further comprising:
a current sensing circuit configured to measure a first current through the selected channel when the selected channel is closed and the plurality of unselected channels is open, and a second current when the selected channel is closed and the plurality of unselected channels is closed; and a voltage sensing circuit configured to measure a first root mean squared (RMS) voltage applied to the selected channel when the selected channel is closed and the plurality of unselected channels is open, and a second RMS voltage when the selected channel is closed and the plurality of unselected channels is closed.

17. The signal generator of claim 16, wherein the microcontroller is further configured to receive the first current and the second current from the current sensing circuit, and the first RMS voltage and the second RMS voltage from the voltage sensing circuit, and wherein the microcontroller computes the first impedance based on the first current and the first RMS voltage, and the second impedance based on the second current and the second RMS voltage.

18. The signal generator of claim 17 further comprising an RF source configured to transmit a first low-power RF signal over the selected channel for the purpose of measuring the first current and the first RMS voltage, and transmit a second low-power RF signal over the selected channel for the purpose of measuring the second current and the second RMS voltage.

19. The signal generator of claim 14, wherein the microcontroller is further configured to time-multiplex an RF ablation signal over each of the plurality of channels.

\* \* \* \* \*